United States Patent
Scholz et al.

(10) Patent No.: US 12,238,093 B2
(45) Date of Patent: Feb. 25, 2025

(54) METHODS AND DEVICES FOR GRANTING TEMPORARY REMOTE ACCESS VIA BIOMETRIC DATA

(71) Applicant: Telefonaktiebolaget LM Ericsson (publ), Stockholm (SE)

(72) Inventors: Heike Scholz, Darmstadt (DE); Liisa Talman, Bickenbach (DE); Armin Dittschar, Langen (DE)

(73) Assignee: Telefonaktiebolaget LM Ericsson (publ), Stockholm (SE)

( * ) Notice: Subject to any disclaimer, the term of this patent is extended or adjusted under 35 U.S.C. 154(b) by 261 days.

(21) Appl. No.: 17/773,691

(22) PCT Filed: Nov. 4, 2019

(86) PCT No.: PCT/SE2019/051108
§ 371 (c)(1),
(2) Date: May 2, 2022

(87) PCT Pub. No.: WO2021/091437
PCT Pub. Date: May 14, 2021

(65) Prior Publication Data
US 2022/0385653 A1    Dec. 1, 2022

(51) Int. Cl.
*H04L 9/40* (2022.01)
*G06F 9/451* (2018.01)

(52) U.S. Cl.
CPC ...... *H04L 63/0861* (2013.01); *H04L 63/0492* (2013.01); *G06F 9/452* (2018.02)

(58) Field of Classification Search
CPC .. H04L 63/0861; H04L 63/0492; G06F 9/452
See application file for complete search history.

(56) References Cited

U.S. PATENT DOCUMENTS 8,508,338 B1 * 8/2013 Fiddy ............... G06Q 20/40145
340/5.82
9,942,222 B1    4/2018 Fenton et al.
(Continued)

FOREIGN PATENT DOCUMENTS

| EP | 2192519 A1 | 6/2010 |
| EP | 2606404 A1 | 6/2013 |
| WO | 2016024876 A1 | 2/2016 |

OTHER PUBLICATIONS

International Search Report and Written Opinion issued in International Application No. PCT/SE2019/051108, dated Sep. 9, 2020 (12 pages).

*Primary Examiner* — Ayoub Alata
(74) *Attorney, Agent, or Firm* — Sonoda & Kobayashi Intellectual Property Law; Sarvajit S. Patil (57) ABSTRACT

Methods and devices are provided for granting temporary remote access via biometric data. A method may include establishing, by a content computing device, a communication session between the content computing device and a remote computing device. The method may further include receiving, by the content computing device from a biometric sensor, a signal confirming biometric authentication thereby establishing an authentication session between the content computing device and the biometric sensor. The method may further include granting, by the content computing device, the temporary remote access for the remote computing device to the data stored in a data storage of the content computing device during said communication session and while the authentication session remains valid. The content computing device is configured to be proximate to the biometric sensor.

20 Claims, 8 Drawing Sheets

(56) References Cited

U.S. PATENT DOCUMENTS

| | | |
|---|---|---|
| 2012/0277543 A1 | 11/2012 | Homchowdhury et al. |
| 2013/0091537 A1 | 4/2013 | Parla et al. |
| 2014/0101453 A1 | 4/2014 | Senthurpandi |
| 2016/0012249 A1 | 1/2016 | Keppler |
| 2016/0328522 A1* | 11/2016 | Howley .............. H04L 63/0861 |
| 2017/0177797 A1* | 6/2017 | Kurniawan ......... H04L 63/0861 |

* cited by examiner

Communicate to content computing device, a signal confirming biometric authentication to thereby establish authentication session, wherein temporary remote access is to data stored in data storage of content computing device and is granted to remote computing device during communication session between content computing device and remote computing device and while authentication session remains valid, wherein biometric sensor configured to be proximate to content computing device.

METHODS AND DEVICES FOR GRANTING TEMPORARY REMOTE ACCESS VIA BIOMETRIC DATA

CROSS REFERENCE TO RELATED APPLICATION(S)

This application is a 35 U.S.C. § 371 National Stage of International Patent Application No. PCT/SE2019/051108, filed Nov. 4, 2019.

TECHNICAL FIELD

The present invention generally relates to communication networks and, more particularly, to mechanisms and techniques for granting temporary remote access via biometric data.

BACKGROUND

Remote access technologies allowing one computing device to access another computing device can be useful in many situations. For example, a worker may use remote access software such as AnyDesk™ or TeamViewer™ to remotely access a desktop computing device located in the worker's office. According to one approach, the worker may install software on their office desktop that enables a session to be established between a remote computing device (e.g., the worker's home computer, laptop, tablet, smartphone) and the worker's desktop computing device. To establish such a session, a user of the remote computing device may use a common browser or run an easily downloadable application to establish a session between the remote computing device and the office desktop computing device. Once the session is established, a user of the remote computing device may "see" or access the office desktop computing device. For example, the remote computing device may display the operating system user interface of the office desktop computing device and allow the user of the remote computing device to use the office desktop computing device.

One skilled in the art will appreciate the usefulness and desirability of such remote access technologies, not just for a worker accessing their office desktop, but in other situations where it may be beneficial for a remote computing device to remotely access or control another computing device. For example, it may be useful and desirable for a technical support professional to access a customer's computer, or for triggering data downloads. As yet another example, it may be useful and desirable for a service provider who needs to review user-side content to be given remote access to the user's computer.

Using such remote access technologies allows a remote user to have up to full access including control of another computer, which provides benefits, but also exposes the content and data of the accessed computer. Needless to say, security may be a consideration in remote access technologies.

Remote access security typically utilizes temporary passwords, unique identities, and encryption. According to one approach, a centralized server may provide encrypted paths between a computing device to be accessed and a remote computing device. A unique identity of the computing device to be accessed along with a temporary password may be required to be entered into remote computing device. However even these security techniques may not be sufficient to safeguard highly sensitive data from being improperly remotely accessed. More detailed examples of problem scenarios are provided below.

In view of the problems discussed herein, there is a need to provide methods and systems that overcome drawbacks associated with granting remote access.

SUMMARY

Embodiments allow for securely granting temporary remote access via biometric data. These embodiments can be advantageous by ensuring more secure access of a content computing device where an access grant may be conditioned on proximity of a biometric sensor to the content computing device, and receipt by the content computing device of a biometric authentication signal from the biometric sensor.

According to an embodiment, there is a method of a content computing device to enable temporary remote access to data stored in the content computing device using biometric data for authentication. The method may include establishing, by a content computing device, a communication session between the content computing device and a remote computing device. The method may further include receiving, by the content computing device from a biometric sensor, a signal confirming biometric authentication thereby establishing an authentication session between the content computing device and the biometric sensor. The method may further include granting, by the content computing device, the temporary remote access for the remote computing device to the data stored in a data storage of the content computing device during said communication session and while the authentication session remains valid. The content computing device may be configured to be proximate to the biometric sensor.

According to an embodiment, there is a method of a biometric sensor to enable temporary remote access using biometric data for authentication. The method may include communicating to a content computing device, a signal confirming biometric authentication to thereby establish an authentication session. The temporary remote access may be to data stored in a data storage of the content computing device and may be granted to a remote computing device during a communication session between the content computing device and the remote computing device and while the authentication session remains valid. The biometric sensor may be configured to be proximate to the content computing device.

According to an embodiment, there is a content computing device configured to enable temporary remote access to data stored in the content computing device using biometric data for authentication. The content computing device may include a processor a data storage including the data stored therein. The processor may be configured to establish, by the content computing device, a communication session between the content computing device and a remote computing device. The processor may further be configured to receive, by the content computing device from a biometric sensor, a signal confirming biometric authentication thereby establishing an authentication session between the content computing device and the biometric sensor. The processor may further be configured to grant, by the content computing device, the temporary remote access for the remote computing device to the data stored in the data storage during said communication session and while the authentication session remains valid. The content computing device is configured to be proximate to the biometric sensor.

According to an embodiment, there is a biometric sensor to enable temporary remote access using biometric data for authentication. The biometric sensor may include an output configured to communicate to a content computing device, a signal confirming biometric authentication to thereby establish an authentication session. The temporary remote access may be to data stored in a data storage of the content computing device and may be granted to a remote computing device during a communication session between the content computing device and the remote computing device and while the authentication session remains valid. The biometric sensor may be configured to be proximate to the content computing device.

According to an embodiment, there is a computer-readable storage medium containing a computer-readable code that when read by a processor causes the processor to perform a method of a content computing device to enable temporary remote access to data stored in the content computing device using biometric data for authentication. The method may include establishing, by a content computing device, a communication session between the content computing device and a remote computing device. The method may further include receiving, by the content computing device from a biometric sensor, a signal confirming biometric authentication thereby establishing an authentication session between the content computing device and the biometric sensor. The method may further include granting, by the content computing device, the temporary remote access for the remote computing device to the data stored in a data storage of the content computing device during said communication session and while the authentication session remains valid. The content computing device may be configured to be proximate to the biometric sensor.

According to an embodiment, there is a computer-readable storage medium containing a computer-readable code that when read by a processor causes the processor to perform a method of a biometric sensor to enable temporary remote access using biometric data for authentication. The method may include communicating to a content computing device, a signal confirming biometric authentication to thereby establish an authentication session. The temporary remote access may be to data stored in a data storage of the content computing device and may be granted to a remote computing device during a communication session between the content computing device and the remote computing device and while the authentication session remains valid. The biometric sensor may be configured to be proximate to the content computing device.

According to an embodiment, there is an apparatus that may be adapted to establish, by the apparatus, a communication session between the apparatus and a remote computing device. The apparatus may be adapted to receive, by the apparatus from a biometric sensor, a signal confirming biometric authentication thereby establishing an authentication session between the apparatus and the biometric sensor. The apparatus may be adapted to grant, by the apparatus, the temporary remote access for the remote computing device to the data stored in a data storage of the apparatus during said communication session and while the authentication session remains valid. The apparatus may be configured to be proximate to the biometric sensor.

According to an embodiment, there is an apparatus that may be adapted to communicate to a content computing device, a signal confirming biometric authentication to thereby establish an authentication session. The temporary remote access may be to data stored in a data storage of the content computing device and may be granted to a remote computing device during a communication session between the content computing device and the remote computing device and while the authentication session remains valid. The apparatus may be configured to be proximate to the content computing device.

According to an embodiment, there is an apparatus. The apparatus may include a first module configured to establish, by the apparatus, a communication session between the apparatus and a remote computing device. The apparatus may further include a second module configured to receive, by the apparatus from a biometric sensor, a signal confirming biometric authentication thereby establishing an authentication session between the apparatus and the biometric sensor. The apparatus may further include a third module configured to grant, by the apparatus, the temporary remote access for the remote computing device to the data stored in a data storage of the apparatus during said communication session and while the authentication session remains valid. The apparatus may be configured to be proximate to the biometric sensor.

According to an embodiment, there is an apparatus. The apparatus may include a module configured to communicate to a content computing device, a signal confirming biometric authentication to thereby establish an authentication session. The temporary remote access may be to data stored in a data storage of the content computing device and may be granted to a remote computing device during a communication session between the content computing device and the remote computing device and while the authentication session remains valid. The apparatus may be configured to be proximate to the content computing device.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

In the following description, for purposes of explanation and non-limitation, specific details are set forth, such as particular nodes, functional entities, techniques, protocols, standards, etc. in order to provide an understanding of the described technology. It will be apparent to one skilled in the art that other embodiments may be practiced apart from the specific details disclosed below. In other instances, detailed descriptions of well-known methods, devices, techniques, etc. are omitted so as not to obscure the description with unnecessary detail. Individual function blocks are shown in the figures, including e.g., a biometric sensor. Those skilled in the art will appreciate that the operations/functions of those blocks may be implemented using individual hardware circuits, using software programs and data in conjunction with a suitably programmed microprocessor or general purpose computing device, using applications specific integrated circuitry (ASIC), and/or using one or more digital signal processors (DSPs). The software program instructions and data may be stored on computer-readable storage medium and when the instructions are executed by a computing device or other suitable processor control, the computing device or processor performs the operations/functions.

Thus, for example, it will be appreciated by those skilled in the art that block diagrams herein can represent conceptual views of illustrative circuitry or other functional units embodying the principles of the technology. Similarly, it will be appreciated that any flow charts, state transition diagrams, pseudocode, and the like represent various processes which may be substantially represented in a non-transitory computer readable medium and so executed by a computing device or processor, whether or not such computing device or processor is explicitly shown.

The functions of the various elements including functional blocks, including but not limited to those labeled or described as "computing device", "processor" or "controller" may be provided through the use of hardware such as circuit hardware and/or hardware capable of executing software in the form of coded instructions stored on computer readable medium. Thus, such functions and illustrated functional blocks are to be understood as being hardware-implemented and/or computer-implemented, (e.g., machine-implemented).

In terms of hardware implementation, the functional blocks may include or encompass, without limitation, digital signal processor (DSP) hardware, reduced instruction set processor, hardware (e.g., digital or analog) circuitry including but not limited to application specific integrated circuit(s) (ASIC), and (where appropriate) state machines capable of performing such functions.

In terms of computer implementation, a computing device is generally understood to comprise one or more processors, or one or more controllers, and the terms computer, computing device, processor, and controller may be employed interchangeably herein. When provided by a computing device, processor, or controller, the operations/functions may be provided by a single dedicated computing device, processor, or controller, by a single shared computing device, processor, or controller, or by a plurality of individual computing devices, processors, or controllers, some of which may be shared or distributed. Moreover, use of the term "processor" or "controller" shall also be construed to refer to other hardware capable of performing such functions and/or executing software, such as the example hardware recited above.

As described in the Background section, security is a consideration in remote access technologies. A problem with a typical password-based approach is that it may actually be too easy to establish sessions when remote access software is installed on a computing device. A session may be established by a remote computing device when only the identity (and/or network location) and password of the computing device to be accessed is known.

Another problem may arise in situations where it is desirable to have one or more users on both ends of a session between two computing devices. In a service provider example, a user of a computing device to be accessed may have sensitive data that the user would like to share with the service provider but only under certain conditions. For example, the user may only want to reveal their sensitive data to the service provider (e.g., the remote computing device) during a session. The problem that may arise from existing remote access technologies is that presence of a user may not be required at the computing device to be accessed. Even if a user of the computing device is made to press a specific button on their computing device so as to indicate presence, such an indication could be simulated remotely and also could be actually performed by a person other than the authorized user, so long as the person has access to the computing device to be accessed.

Embodiments described herein provide devices and methods for granting temporary remote access via biometric data. Accordingly, embodiments enable temporary remote access by a remote computing device only if an authorized user to a computing device to be accessed (e.g., a content computing device) grants access explicitly via biometric data authentication proximate to the content computing device. Remote access is granted to the remote computing device only if the user of the content computing device is present and starts the session via authentication using biometric data (e.g., fingerprint, voice, or iris recognition). An aspect of this concept may be starting/stopping of the temporary remote access via biometric binding to the physical person.

Figure 1:
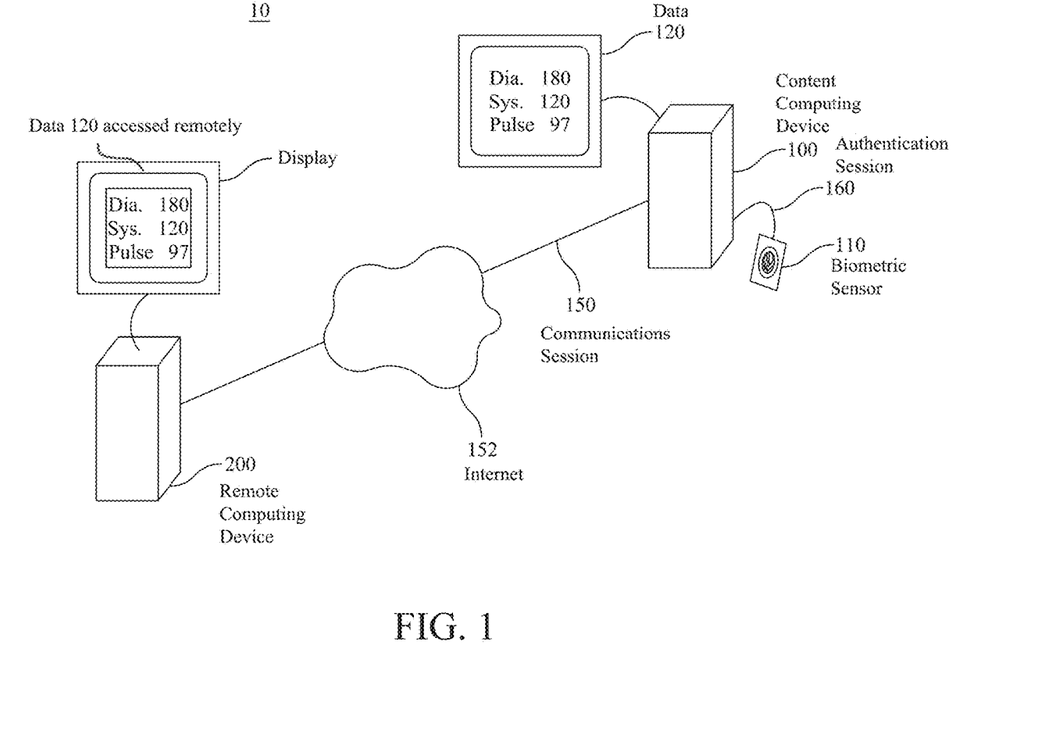
FIG. 1 depicts an architecture which can support various temporary remote access use cases according to an embodiment.
Figure 2:
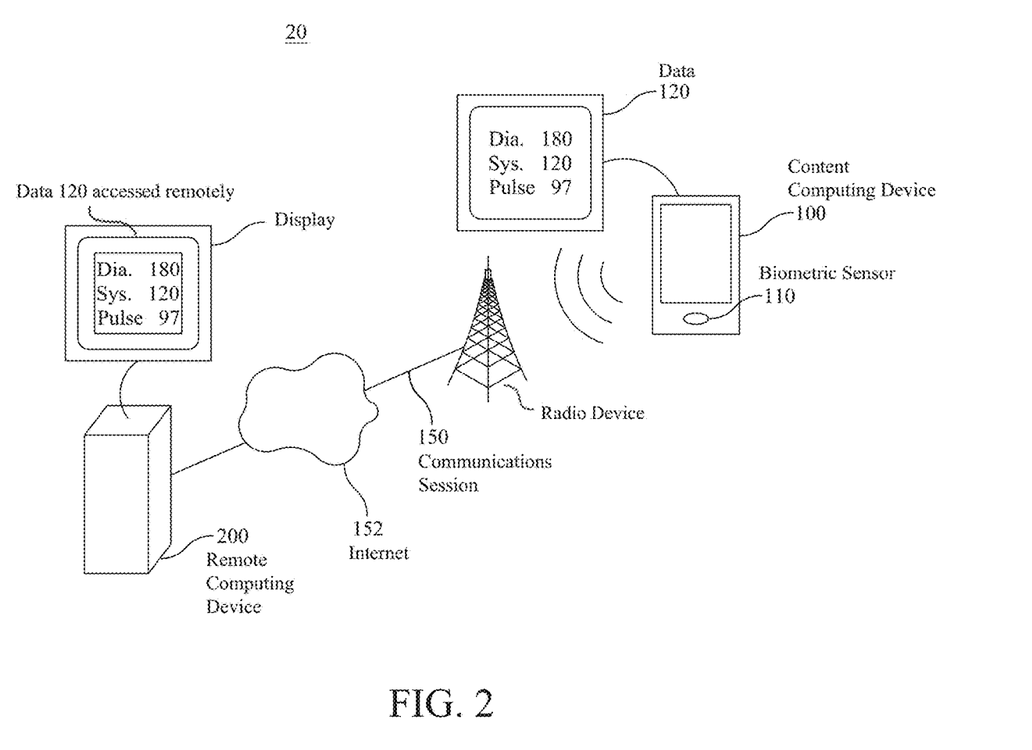
FIG. 2 depicts an architecture which can support various temporary remote access use cases according to another embodiment.

FIGS. 1 and 2 are block diagrams of architectures 10, 20 to grant temporary remote access via biometric data according to exemplary embodiments. Elements of the architectures 10, 20 are described in conjunction with FIGS. 1 and 2. Operations of the elements of FIGS. 1 and 2 are described in conjunction with FIGS. 3 and 4, which depict operations of certain elements of FIGS. 1 and 2. Later, an exemplary use scenario is described with reference to FIGS. 5A and 5B.

Turning to FIG. 1, an architecture 10 may include a content computing device 100 in communication with a biometric sensor 110. As discussed in more detail herein, a session 150 may be established between the content computing device 100 and a remote computing device 200 enabling communication between the content computing device 100 and the remote computing device 200. For example, the content computing device 100 and the remote computing device 200 may be capable of communications via a communications network such as the Internet 152.

The content computing device 100 may enable temporary remote access to data stored in the content computing device 100 using biometric data for authentication. The content computing device 100 may be a desktop computing device as shown in FIG. 1. Those skilled in the art will appreciate that the content computing device 100 may be embodied in many forms, including as shown in FIG. 2, user equipment (UE) such as a smartphone, a tablet computing device, or a laptop. Aspects of the content computing device 100 may be similar to the computing device 610 shown with respect to the exemplary and nonlimiting computing system environment of FIG. 6.

The content computing device 100 may include a processor and a data storage containing data 120 such as sensitive data. As shown in FIGS. 1 and 2, the data 120 may include protected health information such as a patient's blood pressure values and a pulse value. However, those skilled in the art will appreciate that the sensitive data may include many different types of sensitive data. For example, sensitive data may include financial information such as credit card numbers, confidential or privileged information such as attorney/client privileged information, evidence, or social security numbers. The data storage may include appropriate hardware as discussed herein and as known to those skilled in the art, and may include files protected by password, encryption, and/or additional security techniques.

The content computing device 100 may be in communication with and/or include a biometric sensor 110 such as a fingerprint scanner. Biometric sensors 110 are discussed in detail herein. The content computing device 100 may be configured to be proximate to the biometric sensor. "Proximate" as used herein may be interpreted as physically located near another object as determined by those of skilled in the art, considering the embodiment in question. For example, "proximate" may include 1 meter or less, 10 meters or less, 100 meters or less, 1000 meters or less, or less, or another appropriate value, as determined by those skilled in the art, considering the embodiment in question. Moreover, according to an embodiment, the proximity between the content computing device 100 and the biometric sensor 110 is determined, at least in part, based on a distance which enables a secure, direct, point-to-point communication link to be established between the content computing device 100 and the biometric sensor 110, examples of which are described below.

In an embodiment, the content computing device 100 may be configured to be connected with the biometric sensor 110 by a wired connection between the content computing device 100 and the biometric sensor 110. For example, the content computing device 100 may include a special purpose port to receive a wired connection to the biometric sensor. As another example, the content computing device 100 may include a USB port to receive a USB biometric sensor such as a USB fingerprint sensor. The wired connection may ensure proximity between the computing device 100 and the biometric sensor 110.

In another embodiment, the content computing device 100 may be configured to be connected to the biometric sensor 110 by a direct point-to-point wireless connection between the content computing device 100 and the biometric sensor 110. "Direct point-to-point wireless" should be interpreted to include varying technologies. For example, the content computing device 100 and the biometric sensor 110 may each be configured as endpoints communicating with each other via a point-to-point wireless connection, via radio or line of sight. As another example, the content computing device and the biometric sensor 110 may be configured to communicate via nearfield communication. Yet another embodiment involves a cellphone (as a biometric sensor) using Bluetooth communication to connect to the content computing device 100. The direct point-to-point wireless connection may ensure proximity between the computing device 100 and the biometric sensor 110.

In another embodiment, the content computing device 100 may further comprise the biometric sensor integrated therein as shown in FIG. 2. The integration of the biometric sensor 110 into the content computing device 100 may ensure proximity between the computing device 100 and the biometric sensor 110.

Figure 3:
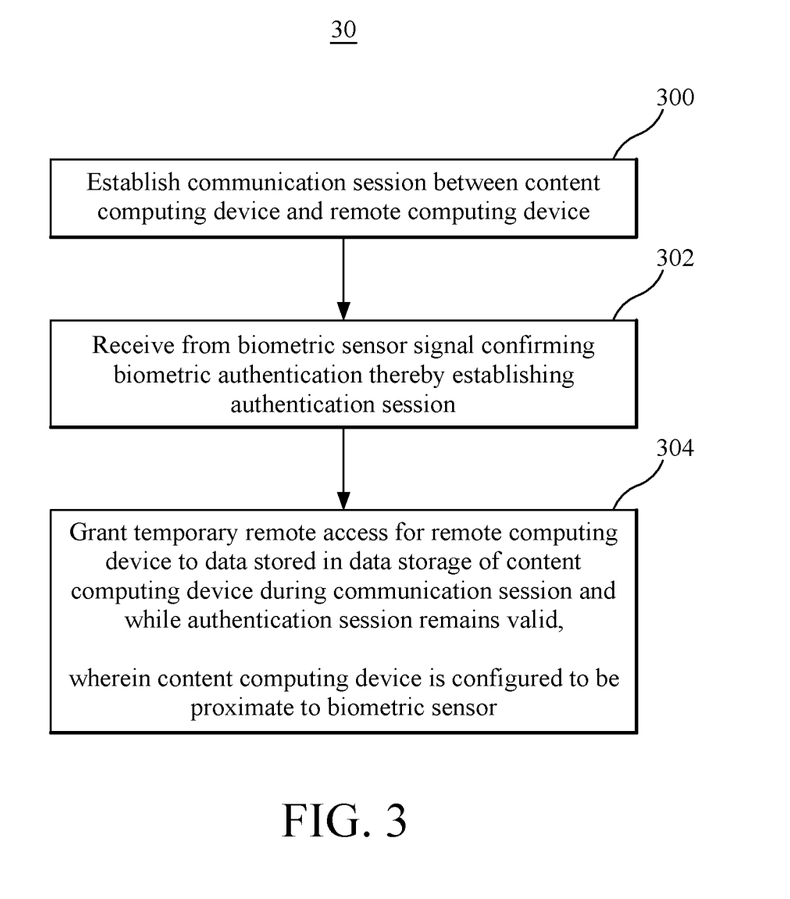
FIG. 3 shows a flowchart of a method of a content computing device to enable temporary remote access to data stored in the content computing device using biometric data for authentication according to an embodiment.

The processor of the content computing device 100 may be configured to perform operations (e.g., by instructions) including, e.g., a session establishment operation, an authentication confirmation operation, and an access granting operation, all shown in FIG. 3. More specifically, FIG. 3 is a flowchart of a method 30 of the content computing device 100 to enable temporary remote access to the data stored in the content computing device 100 using biometric data for authentication.

In operation 300, the method 30 may establish, by the content computing device 100, the communication session 150 between the content computing device 100 and the remote computing device 200. For example, a secure communication session may be established between the content computing device 100 and the remote computing device 200 using an encrypted communication session. Establishment of the communication session 150 may involve authentication of the remote computing device 200 by the content computing device 100 and authentication of the content computing device 100 by the remote computing device 200. For example, authentication may involve mutual challenge-response authentication of the content computing device 100 and the remote computing device 200.

In operation 302, the method 30 may receive from the biometric sensor 110, a signal confirming biometric authentication thereby establishing an authentication session 160 (shown in FIG. 1) between the content computing device 100 and the biometric sensor 110. In an embodiment, the authentication session 160 may be temporally limited. A timeout value may be stored in the content computing device 100 and/or the biometric sensor 110. The signal confirming biometric authentication may be embodied in different forms In one embodiment, the content computing device 100 may receive (as the signal confirming biometric authentication) from the biometric sensor 110, biometric data for comparison of the biometric data with a reference. That is, the biometric data is received from the biometric sensor 110. The content computing device 100 may include a secure storage of reference biometric data. The reference biometric data may be stored such that only operations related to comparison of the biometric data have access to said reference biometric data. The operations related to comparison may be accessible to or in conjunction with the biometric sensor such that the stored reference biometric data is physically separate from the biometric scanner, but logically part of the biometric scanner. For example, in a fingerprint scanner embodiment, the content computing device 100 may receive the data from the fingerprint scan and the content computing device 100 may compare the data with reference data stored on the content computing device 100. As another example, the content computing device 100 may receive a subset of the data from the fingerprint scan. Stated differently, a subset of the biometric data may be received from the biometric sensor 110. In another example where multiple signals confirming biometric authentication are received, an initial signal may comprise the biometric data and one or more subsequent signals may comprise one or more subsets of biometric data.

For example, in an embodiment where fingerprint biometric data is used for authentication, the biometric scanner 110 may identify various fingerprint features (e.g., recurves, ridges, a delta, scars, creases, etc.) to generate a first set of fingerprint features which provide sufficient information to accurately identify the user associated with the sensed biometric data and can send the entire first set of fingerprint features to the content computing device 100 as the biometric authentication signal.

In another embodiment, the content computing device 100 may receive (as the signal confirming biometric authentication) a signal confirming biometric authentication from the biometric sensor 110. The signal confirming biometric authentication should be different for each session to avoid replay attacks. In other words, a result of a comparison by the biometric sensor 110 may be received from the biometric sensor 110 in the content computing device 100. For example, in a fingerprint scanner embodiment, the content computing device 100 may receive from a fingerprint scanner, a signal sent as a result of a successful comparison of the fingerprint scan with reference data stored on the biometric scanner. The signal may include a subset of the biometric data collected by the biometric sensor 110. Using the earlier example, if the biometric sensor collects a first set of fingerprint features which provide sufficient information to accurately identify the user associated with the sensed biometric data, i.e., fingerprint features such as recurves, ridges, a delta, scars, creases, etc, instead of sending the entire first set of fingerprint features, the biometric sensor 110 can send a second, subset of the first set as part of the biometric authentication signal to the content computing device 100.

According to yet another embodiment, the biometric data is hashed first and only the hash is sent to the computing device 100, so that the biometric data itself is not known by the computing device 100. Thus, as used herein, the term "biometric data" includes both the raw biometric data itself, a subset of the raw biometric data and/or a hash of the biometric data.

In one or more embodiments, the authentication session between the content computing device 100 and the biometric sensor 110 may be encrypted. For example, encryption keys such as private encryption keys may reside one or both of the content computing device 100 and the biometric sensor 110. The content computing device 100 and the biometric sensor 110 may use an asymmetric encryption algorithm to establish the authentication session 160.

In operation 304, the method 30 may grant the temporary remote access for the remote computing device 200 to the data 120 stored in the data storage of the content computing device 100 during said communication session 150 and while the authentication session 160 remains valid. The authentication session 160 may become invalid (e.g., be terminated) according to one or more techniques.

For example, in an embodiment where the authentication session 160 is temporally limited, the authentication session may be terminated upon temporal expiration unless another signal confirming continued biometric authentication is received by the content computing device 100 from the biometric sensor 110. For example, a series of "keep-alive" signals may need to be received from the biometric sensor 110 by the content computing device 100 to keep the authentication session 160 active (e.g., to prevent termination of the authentication session 160), e.g., one keep-alive signal every X seconds. As with the initial biometric authentication signal, each keep-alive signal may also include biometric data, e.g., a first full set of biometric data or a second subset of biometric data or a hash of either the full set or a subset of the biometric data.

As another example, another signal confirming biometric authentication may be received by the content computing device 100 from the biometric sensor 110. In this embodiment, this second signal may terminate the authentication session 160 when received after the first signal establishing the authentication session 160. For example, an authorized user may scan his or her fingerprint (biometric data) to establish the authentication session 160 and the authorized user may scan his or her fingerprint (biometric data) to terminate the authentication session 160. In an alternative embodiment, more than one biometric sensor 110 may be used. For example, a first biometric sensor may be used to establish an authentication session while a second biometric sensor may be used to terminate an authentication session.

As another example, the signal confirming biometric authentication and granting the authentication session is only received while the biometric sensor is in use. In this embodiment, the authentication session 160 may only be valid while the content computing device 100 is receiving the signal only while the biometric sensor 110 is in use. For example, the authorized user's fingerprint (biometric data) may have to remain on the fingerprint scanner (biometric sensor). Removal of the fingerprint from the scanner may terminate the authentication session 160, e.g., by having the sensor to stop sending the "keep-alive" signals or sending an explicit termination signal when the fingerprint is no longer detected by the scanner.

Figure 5A:
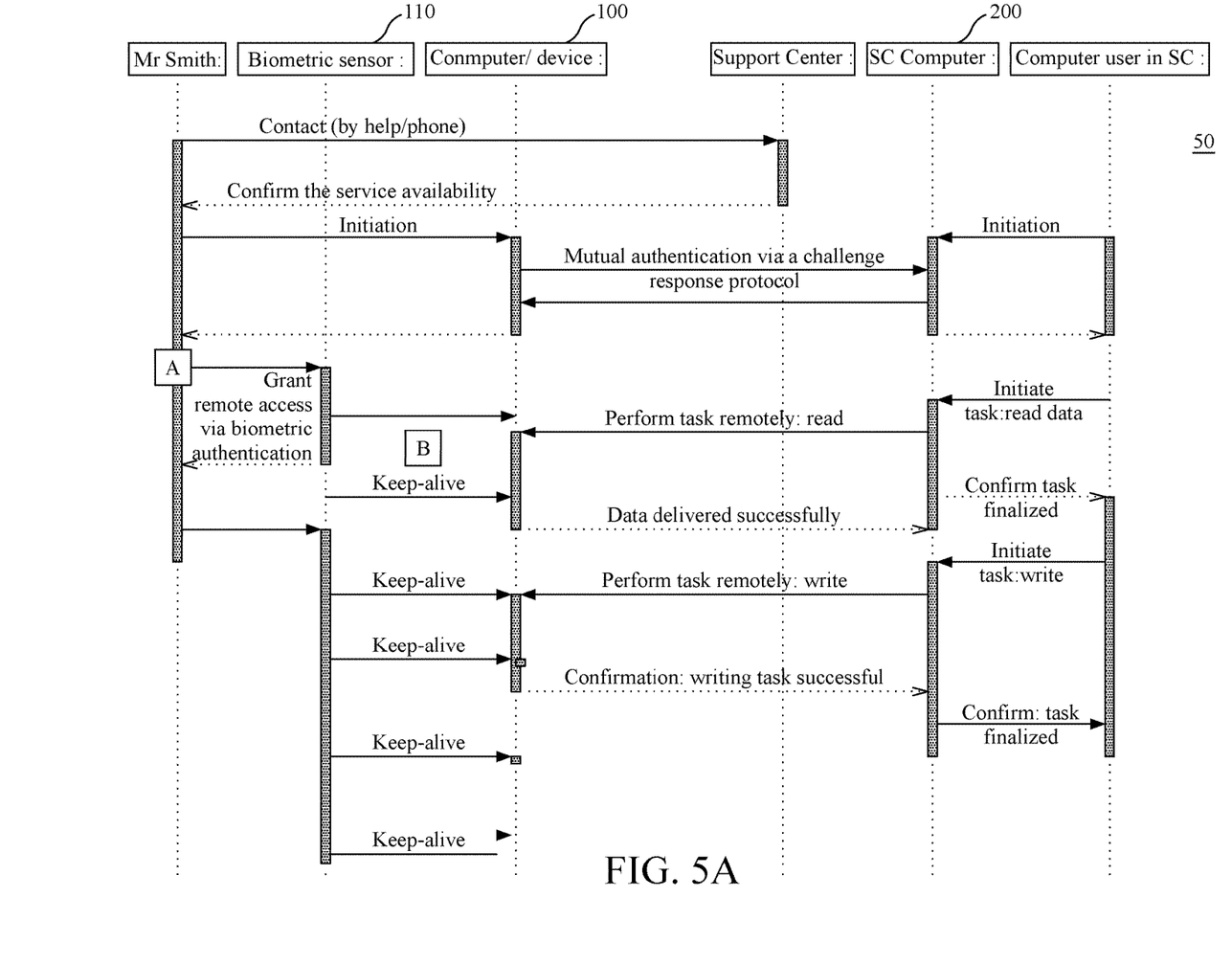
FIGS. 5A and 5B are a signaling diagram of an exemplary use scenario of the described architectures and methods to grant temporary remote access via biometric data according to an embodiment.
Figure 5B:
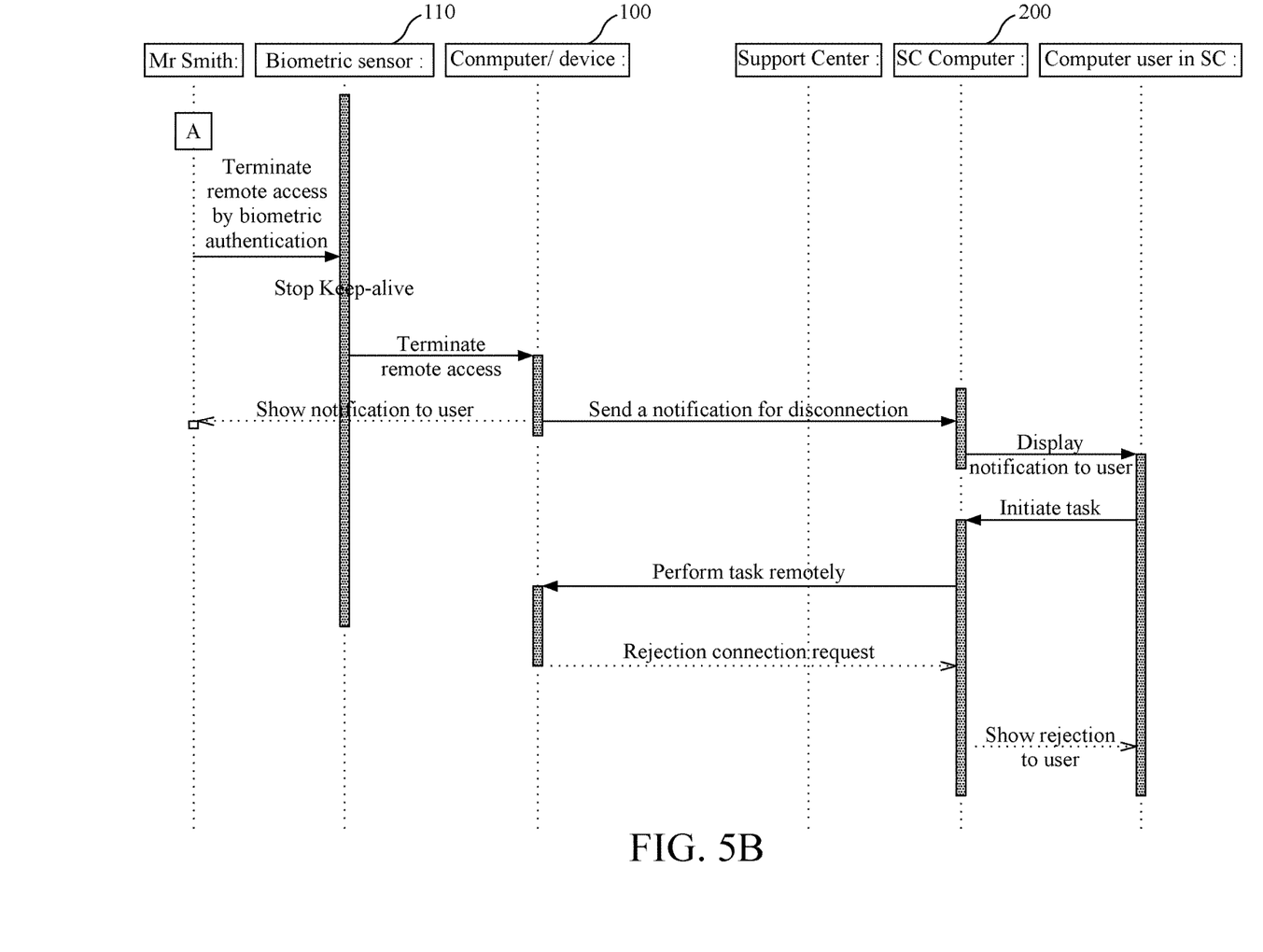

As yet another example, techniques for validating or invalidating the authentication session may be combined, as discussed herein with reference to the use example of FIGS. 5A and 5B.

Accordingly, a content computing device 100 configured to enable temporary remote access to data stored in the content computing device 100 using biometric data for authentication is provided, as is a method 30 of the content computing device.

As shown in FIG. 1, the biometric sensor 110 may enable temporary remote access using biometric data for authentication. The biometric sensor 110 may be a fingerprint sensor as shown in FIG. 1. Those skilled in the art will appreciate that the biometric sensor 110 may be embodied in many forms, including as hardware and/or software configured for facial recognition, iris recognition, speech recognition, hand recognition, signature verification, and gait authentication. That is, the biometric sensor 110 may be embodied as a facial recognition camera, an iris scanner, a speech recognizer, a hand recognition device, a signature recognition device, or a gait recognizer. Aspects of the biometric sensor 110 may be similar to the computing device 610 shown with respect to the exemplary and nonlimiting computing system environment of FIG. 6.

The biometric sensor 110 may include hardware for sensing biometric data and may include and/or be communication with logic configured to compare currently sensed biometric data with a stored reference of the biometric data. The biometric sensor 110 may include an output configured to communicate to the content computing device 100, a signal confirming biometric authentication to thereby establish an authentication session 160. For example, a fingerprint sensor 110 may include capacitive sensing hardware or optical hardware. The fingerprint sensor 110 may be in communication with logic and/or include logic, said logic being embodied as instructions resulting in a comparison of a fingerprint scan with a stored reference and outputting of the signal confirming biometric authentication.

Figure 4:
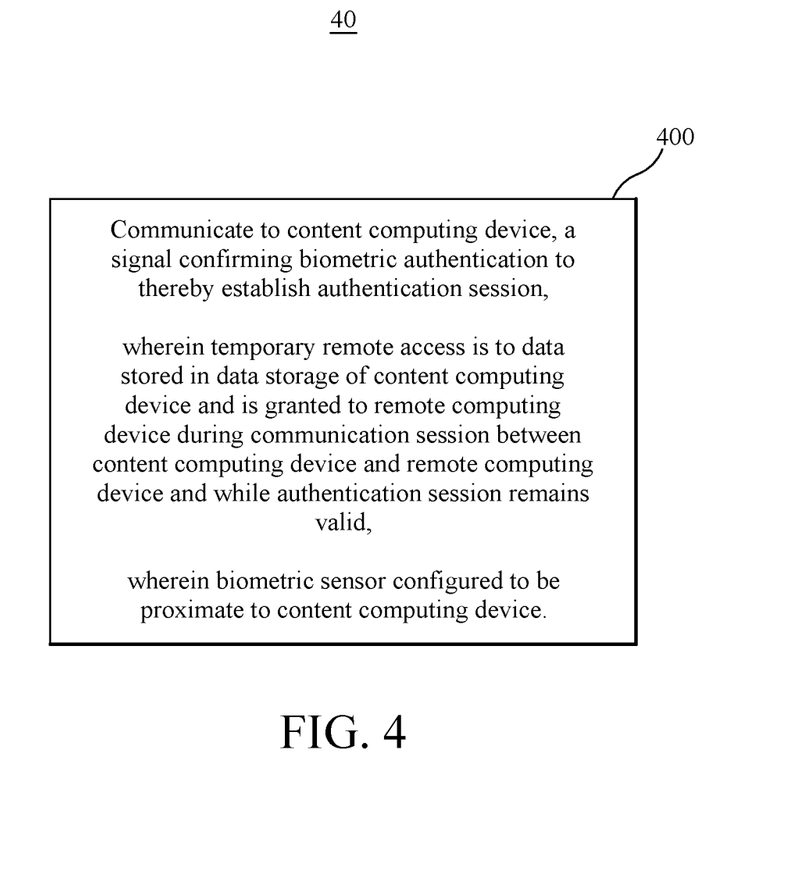
FIG. 4 shows a flowchart of a method of a biometric sensor to enable temporary remote access using biometric data for authentication according to an embodiment.

The biometric sensor 110 may include an output configured to communicate a signal confirming biometric authentication to the content computing device 100. FIG. 4 is a flow chart of a method 40 of the biometric sensor 110 to enable temporary remote access using biometric data for authentication, and includes operation 400 of communicating to the content computing device 100, a signal confirming biometric authentication to thereby establish the authentication session 160.

For example, the biometric sensor 110 according to one embodiment may include a processor and memory and may be configured to compare biometric data to a stored reference. For example, a fingerprint scanner 110 may compare a fingerprint scan with a stored reference and communicate an authorization to the content computing device 100 provided the fingerprint scan and the stored reference match. In an embodiment, the biometric sensor 110 may communicate a non-authorization to the content computing device if the biometric data and the stored reference fail to match.

The temporary remote access may be to data such as the sensitive data 120 stored in the data storage of the content computing device 110. The temporary remote access may be granted to a remote computing device 200 only during a communication session 150 between the content computing device 100 and the remote computing device 200 and while the authentication session 160 remains valid.

FIGS. 5A and 5B are a signaling diagram of an exemplary use scenario of the described architectures and methods to grant temporary remote access via biometric data. According to this exemplary and non-limiting scenario, a service provider (e.g., "User in SC" (Support Center)) using a remote computing device 200 (e.g., "SC Computer") is a physician using the remote computing device 200 to view protected health information stored on a patient user's (e.g., "Mr. Smith's") content computing device 100 (e.g., "Computer/device"). The physician may want to check Mr. Smith's blood pressure and pulse values, and may want to change Mr. Smith's medicine dosing.

Mr. Smith's content computing device 100 may be a device having healthcare functionalities (e.g., blood pressure and pulse measuring capabilities and medicine dosing functionalities). Mr. Smith's content computing device 100 may include network communications functionality to communicate over a network such as the Internet 152 with the remote computing device 200 of the physician's office (e.g., "Support Center"). Mr. Smith's content computing device 100 may include a storage having blood pressure and pulse measurements, as well as medicine dosing instructions stored thereon (e.g., data or sensitive data 120).

Mr. Smith may contact his physician at the physician's office/medical support center, e.g., via telephone or by selecting a "help" selection e.g., on Mr. Smith's device to communicate that Mr. Smith would like to share the data. The physician may confirm availability of remote access service. Mr. Smith may confirm to the content computing device 100 that a session should be established between the content computing device 100 and the physician's remote computing device 200. For example, Mr. Smith may use his content computing device 100 to initiate the communications session 150 between the content computing device 100 and the remote computing device 200. The physician may use their remote computing device 200 as part of the initiation of the communications session 150. The communications session may be a secure communication session 150 and may involve mutual authentication via a challenge response protocol. Accordingly, in operation 300, Mr. Smith's content computing device 100 may establish the communication session 150 between the content computing device 100 and the physician's remote computing device 200.

According to embodiments, Mr. Smith may have to be present to explicitly grant access to sensitive data 120 stored in the storage of his content computing device 100. This may be realized by requiring Mr. Smith's biometric data. Mr. Smith's content computing device 100 may be in communication with and/or include the biometric sensor 110. For example, a fingerprint scanner may be in communication with and/or integrated with Mr. Smith's device 100. As described herein, Mr. Smith's content computing device 100 and/or the biometric sensor 110 may be configured to be proximate to each other. In operation 302, Mr. Smith's content computing device 100 may receive from the biometric sensor 110, a signal confirming biometric authentication thereby establishing authentication session 160 between the content computing device 100 and the biometric sensor 110. From the perspective of the biometric sensor 110, the signal confirming biometric authentication to thereby establish the authentication session 160 may be output in operation 400.

As discussed herein, the signal confirming biometric authentication may include biometric data (either full or partial) for comparison with a reference by the content computing device 100, or may include a signal confirming a successful comparison by the biometric sensor 110. Upon successful comparison or receipt of a signal indicating such, the authentication session 160 may be established. In an embodiment, Mr. Smith's fingerprint (e.g., "biometric data") may be encrypted and checked on the content computing device 100 using asymmetric encryption.

Access to Mr. Smith's sensitive data may be granted to the physician's remote computing device 200. That is, in operation 304, the content computing device 100 may grant the temporary remote access to the remote computing device 200 to the data 120 stored in the data storage of the content computing device 100 during the communication session 150 and while the authentication remains valid. The physician's remote computing device 200 may download, view or otherwise access the data 120 (e.g., Mr. Smith's blood pressure and pulse values).

In FIGS. 5A and 5B, the initial grant of access and and/or the initial signal confirming biometric authentication, may be represented by reference character "A". As noted herein, the remote access may be temporary. That is, the remote access may be temporally limited. For example, the authentication session may be temporally limited and may be terminated if Mr. Smith explicitly closes the session by, e.g., a fingerprint scan, or if a time limit is reached. In this exemplary use scenario, "keep-alive" signals must be periodically received from the biometric sensor 110 to keep the authentication session 160 valid (e.g., to prevent the termination of the authentication session 160). For example, keep-alive signals may need to be received every 1 second or every 5 seconds. Those skilled in the art will recognize that many possible timeout values may be used. For example, 10 seconds, 30 seconds, 1 minute, 5 minutes, etc. may be used as desired. These keep-alive signals may be signals confirming biometric authentication. Keeping of the grant of access active and/or subsequent signals confirming biometric authentication may be represented by reference character "B" in FIGS. 5A and 5B. In the currently described embodiment, the signals may include biometric data or be generated therefrom so as to avoid easy simulation thereof. In an embodiment, the initial signal may contain a complete set of biometric data (e.g., a full fingerprint scan) and subsequent signals may contain a subset thereof (e.g., subset of a fingerprint scan). In other embodiments, complete biometric data may always be received or a subset may always be received. In yet another embodiment, the initial signal may be a subset of biometric data and subsequent signals may be complete sets of biometric data. In one embodiment, the subsequent keep-alive signals may be sent without requiring a further scan while in another embodiment may require a new biometric sensing (e.g., fingerprint scan) for each signal.

During the maintenance of the active grant of access, the physician can view the sensitive data 120 remotely using the remote computing device 200. That is, the physician may retrieve data from Mr. Smith's computing device 100 and the remote computing device 200 may display that data 120 to the physician after Mr. Smith's computing device 100 delivers the data successfully. As shown in FIG. 5A, the physician can initiate writing of new dosing instructions. As shown in FIG. 5B, Mr. Smith may terminate the remote access by receiving a signal confirming biometric authentication. In this embodiment, this signal may terminate sending of keep-alive signals, which may terminate the authentication session and thereby terminate remote access. In an embodiment, Mr. Smith's content computing device 100 may transmit a notification for disconnection to the physician's remote computing device 200 that may be shown to the physician. Mr. Smith's computing device 100 may disable further requests from the remote computing device 200.

As shown in FIG. 5B, when a remote computing device 200 tries to access the content computing device 100 when remote access is not granted as described herein, access may be rejected.

Many other use examples are possible and would fall within the scope of the present inventive concept. For example, a contact at a computer support center may want to access Mr. Jones' computer to help Mr. Jones. Similarly, an automated system at a support center may want to access Mr. Jones computer to download software updates. Mr. Jones may contact the support center and the contact may use their remote computing device 200 to provide support to Mr. Jones content computing device 100. Mr. Jones may use a "help" selection, e.g., via a website of the computer support center to indicate a desire to initiate remote access. Only Mr. Jones may grant access using his computing device 100 after a communications session 150 and an authentication session 160 have been established. A biometric sensor (e.g., an iris scanner) 110 must be used by Mr. Jones to establish and maintain granting of the remote access to remote computing device 200 of the contact at the support center. Remote access may be terminated by either triggering of termination by another iris scan by Mr. Jones, or a stored timeout value being reached. The biometric sensor 110 may recognize that the time limit has been reached and may stop sending biometric based keep-alive signals.

Accordingly, exemplary use scenarios of the described architectures and methods to grant temporary remote access via biometric data are provided.

Those skilled in the art will recognize that the methods described herein can be implemented alternatively or additionally using one or more servers with these servers being distributed in a cloud architecture associated with an operator network. Cloud computing can be described as using an architecture of shared, configurable resources, e.g., servers, storage memory, applications and the like, which are accessible on-demand. Therefore, when implementing embodiments using the cloud architecture, more or fewer resources can be used to perform the architectural functions described in the various embodiments herein.

The embodiments described herein can provide various useful characteristics. For example, embodiments described herein allow for more secure access of a content computing device. Access may be granted and/or maintained only when an authorized user is actually proximate to the content computing device. Only the actual authorized user may be allowed to initiate or maintain (or terminate) remote access because biometric data of the authorized user is required proximate to the content computing device. Continued access is secure when using keep-alive signals to confirm the authentication session in part due to the keep-alive signals being based on or including biometric data. Continued access is secure when using a timeout value so as to guarantee that the session may be closed automatically after a specific period of time has passed even if an explicit termination of the session is not performed.

Figure 6:
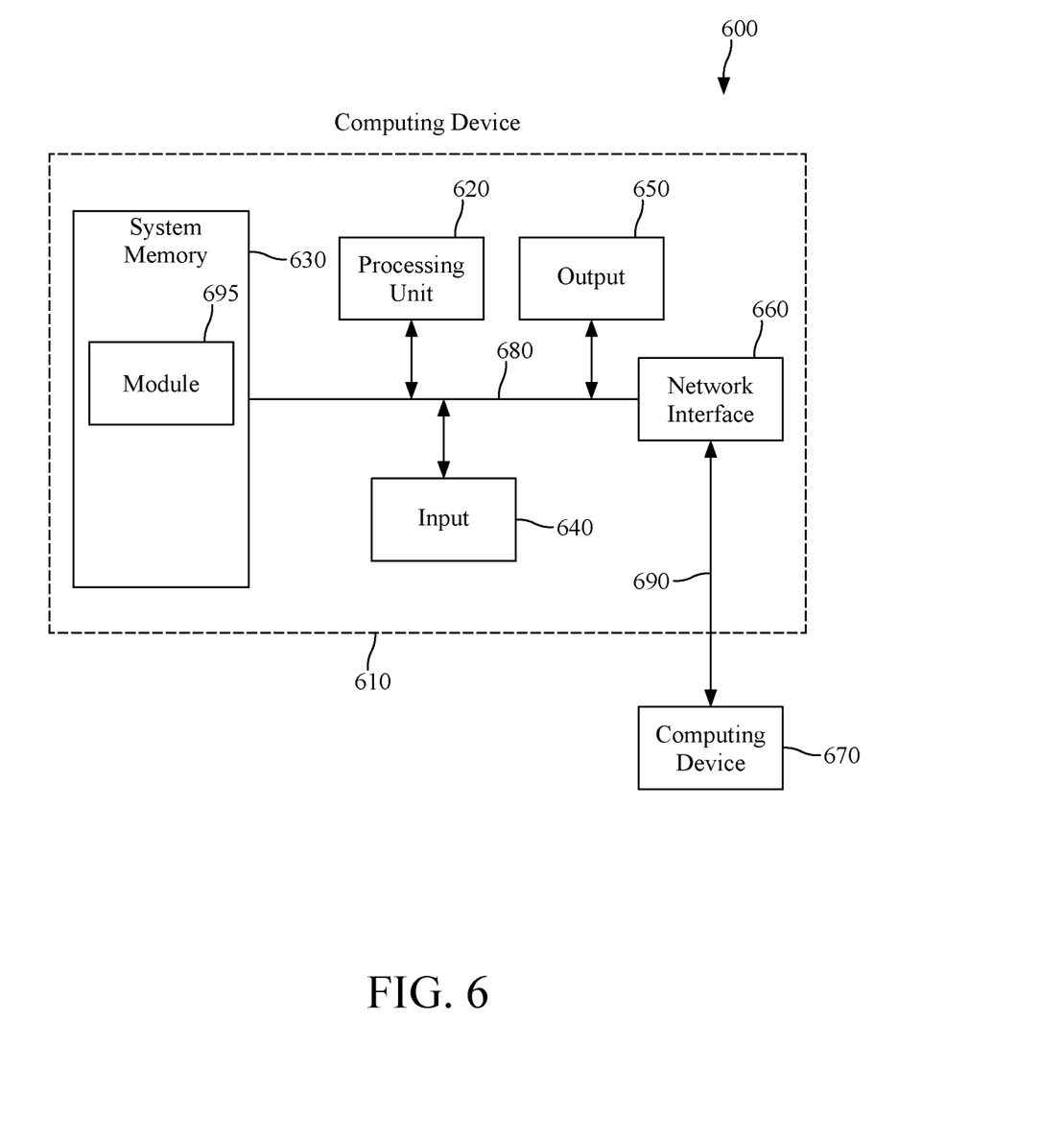
FIG. 6 depicts a computing environment according to an embodiment.

FIG. 6 illustrates an example of a computing environment 600 in which embodiments can be implemented. As noted above, computing system environment 600 is only one example of a suitable computing environment and is not intended to suggest any limitation as to the scope of use or functionality of the claimed subject matter. Further, the computing environment 600 is not intended to suggest any dependency or requirement relating to the claimed subject matter and any one or combination of components illustrated in the various environments/flowcharts described herein.

An example of a device for implementing the previously described devices includes a general purpose computing device 610. Components of computing device 610 can include, but are not limited to, a processing unit 620, a system memory 630, and a system bus 680 that couples various system components including the system memory to the processing unit 620. The system bus 680 can be any of several types of bus structures including a memory bus or memory controller, a peripheral bus, and a local bus using any of a variety of bus architectures.

Computing device 610 can include a variety of transitory and non-transitory computer readable media. Computer readable media can be any available media that can be accessed by computing device 610. By way of example, and not limitation, computer readable media can comprise computer storage media and communication media. Computer storage media includes volatile and nonvolatile as well as removable and non-removable media implemented in any method or technology for storage of information such as computer readable instructions, data structures, program modules or other data. Computer storage media includes, but is not limited to, RAM, ROM, EEPROM, flash memory or other memory technology, CDROM, digital versatile disks (DVD) or other optical disk storage, magnetic cassettes, magnetic tape, magnetic disk storage or other magnetic storage devices, or any other medium which can be used to store the desired information and which can be accessed by computing device 610. Communication media can embody computer readable instructions, data structures, program modules or other data in a modulated data signal such as a carrier wave or other transport mechanism and can include any suitable information delivery media.

The system memory 630 can include computer storage media in the form of volatile and/or nonvolatile memory such as read only memory (ROM) and/or random access memory (RAM). A basic input/output system (BIOS), containing the basic routines that help to transfer information between elements within computing device 610, such as during start-up, can be stored in memory 630. Memory 630 can also contain data and/or program modules that are immediately accessible to and/or presently being operated on by processing unit 620. By way of non-limiting example, memory 630 can also include an operating system, application programs, other program modules, and program data.

The system memory 630 may include a software module 695 loaded in the memory and processable by the processing unit, or other circuitry which cause the system to perform the functions described in this disclosure.

The computing device 610 can also include other removable/non-removable and volatile/nonvolatile computer storage media. For example, computing device 610 can include a hard disk drive that reads from or writes to non-removable, nonvolatile magnetic media, a magnetic disk drive that reads from or writes to a removable, nonvolatile magnetic disk, and/or an optical disk drive that reads from or writes to a removable, nonvolatile optical disk, such as a CD-ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM and the like. A hard disk drive can be connected to the system bus 680 through a non-removable memory interface such as an interface, and a magnetic disk drive or optical disk drive can be connected to the system bus 680 by a removable memory interface, such as an interface.

A user can enter commands and information into the computing device 610 through input devices such as a keyboard or a pointing device such as a mouse, trackball, touch pad, touch screen and/or other pointing device. Other input devices can include a microphone, joystick, game pad, satellite dish, scanner, or similar devices. These and/or other input devices can be connected to the processing unit 620 through user input 640 and associated interface(s) 660 that are coupled to the system bus 680, but can be connected by other interface and bus structures, such as a parallel port, game port or a universal serial bus (USB).

A graphics subsystem can also be connected to the system bus 680. In addition, a monitor or other type of display device can be connected to the system bus 680 through an interface, such as output interface 650, which can in turn communicate with video memory. In addition to a monitor, computers can also include other peripheral output devices, such as speakers and/or printing devices, which can also be connected through output interface 650.

The computing device 610 can operate in a networked or distributed environment using logical connections to one or more other remote computing devices, such as remote computing device 670, which can in turn have media capabilities which are the same or different from computing device 610. The remote computing device 670 can be a personal computer, a server, a router, a network PC, a peer device or other common network node, a UE, and/or any other remote media consumption or transmission device, and can include any or all of the elements described above relative to the computing device 610. The logical connections depicted in FIG. 6 include a network 690, such as a local area network (LAN) or a wide area network (WAN), but can also include other networks/buses.

When used in a LAN networking environment, the computing device 610 may be connected to the LAN 690 through a network interface 660 or adapter. When used in a WAN networking environment, the computing device 610 can include a communications component, such as a modem, or other means for establishing communications over a WAN, such as the Internet. A communications component, such as a modem, which can be internal or external, can be connected to the system bus 680 through the user input interface at input 640 and/or other appropriate mechanism.

Figure 7:
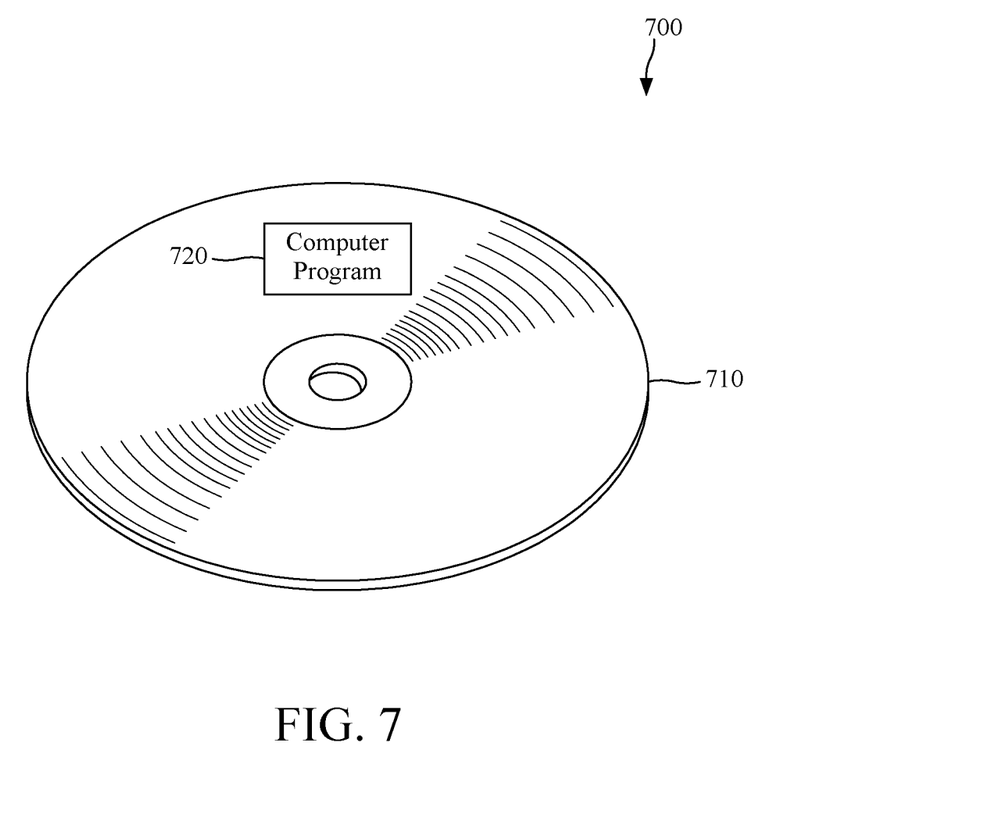
FIG. 7 depicts an electronic storage medium on which computer program embodiments can be stored.

FIG. 7 shows computer readable media 700, e.g., a non-transitory computer readable media, in the form of a computer program product 710 and a computer program product 720 stored on the computer readable medium 700, the computer program capable of performing the functions described herein.

In a networked environment, program modules depicted relative to the computing device 610, or portions thereof, can be stored in a remote memory storage device. It should be noted that the network connections shown and described are exemplary and other means of establishing a communications link between the computers can be used.

Many different embodiments have been disclosed herein, in connection with the above description and the drawings. It will be understood that it would be unduly repetitious and obfuscating to literally describe and illustrate every combination and subcombination of these embodiments. Accordingly, the present specification, including the drawings, shall be construed to constitute a complete written description of various exemplary combinations and subcombinations of embodiments and of the manner and process of making and using them, and shall support claims to any such combination or subcombination.

Many variations and modifications can be made to the embodiments without substantially departing from the principles of the present solution. All such variations and modifications are intended to be included herein within the scope of the present solution.

What is claimed is:

1. A method of a content computing device to enable temporary remote access to data stored in the content computing device using biometric data for authentication, the method comprising:
    establishing, by the content computing device, a communication session between the content computing device and a remote computing device;
    receiving, by the content computing device from a biometric sensor, a signal confirming biometric authentication thereby establishing an authentication session between the content computing device and the biometric sensor;
    granting, by the content computing device, the temporary remote access for the remote computing device to the data stored in a data storage of the content computing device during said communication session and while the authentication session remains valid; and
    receiving, from the biometric sensor, a periodic keep-alive signal confirming that the communication session can continue, wherein the periodic keep-alive signal is received at a regular interval between consecutive receptions thereof,
    wherein the content computing device is configured to be proximate to the biometric sensor or to integrally include the biometric sensor,
    wherein the signal confirming biometric authentication comprises biometric data or a hash of the biometric data, and
    wherein the periodic keep-alive signal comprises a subset of the biometric data less than a full set of the biometric data or a hash of a subset of the biometric data less than a full set of the biometric data.

2. The method of claim 1, wherein the content computing device is configured to be connected with the biometric sensor via a wired connection with the content computing device, or in a direct point-to-point wireless connection with the content computing device.

3. The method of claim 1, wherein the content computing device is configured to integrally include the biometric sensor.

4. The method of claim 1, wherein the establishing of the communication session between the content computing device and the remote computing device comprises a challenge-response authentication.

5. The method of claim 1, wherein the authentication session is temporally limited.

6. The method of claim 1, further comprising:
receiving from the biometric sensor, another signal confirming biometric authentication thereby terminating the authentication session.

7. The method of claim 1, wherein the periodic keep-alive signal is received only while the biometric sensor detects an owner of the content computing device's biometric input.

8. A method of a biometric sensor to enable temporary remote access using biometric data for authentication, the method comprising:
communicating to a content computing device, a signal confirming biometric authentication to thereby establish an authentication session, wherein:
the temporary remote access is access to data stored in a data storage of the content computing device and is granted to a remote computing device during a communication session between the content computing device and the remote computing device and while the authentication session remains valid,
the biometric sensor is configured to be proximate to the content computing device or to be integrated with the content computing device, and
the authentication session is terminated unless renewed by the biometric sensor communicating a periodic keep-alive signal confirming that the communication session can continue, wherein the periodic keep-alive signal is communicated at a regular interval between consecutive communications thereof,
wherein the signal confirming biometric authentication comprises biometric data or a hash of the biometric data, and
wherein the periodic keep-alive signal comprises a subset of the biometric data less than a full set of the biometric data or a hash of a subset of the biometric data less than a full set of the biometric data.

9. The method of claim 8, wherein the biometric sensor is configured to be connected to the content computing device via a wired connection with the content computing device, or in a direct point-to-point wireless connection with the content computing device.

10. The method of claim 8, wherein the biometric sensor is configured to be integrated with the content computing device.

11. The method of claim 8, wherein the authentication session is temporally limited.

12. The method of claim 8, further comprising:
communicating to the content computing device, another signal confirming biometric authentication thereby terminating the authentication session.

13. The method of claim 8, wherein the periodic keep-alive signal is received only while the biometric sensor detects an owner of the content computing device's biometric input.

14. A content computing device configured to enable temporary remote access to data stored in the content computing device using biometric data for authentication, the content computing device comprising:
a processor; and
a data storage including the data stored therein,
wherein the processor is configured to:
establish, by the content computing device, a communication session between the content computing device and a remote computing device;
receive, by the content computing device from a biometric sensor, a signal confirming biometric authentication thereby establishing an authentication session between the content computing device and the biometric sensor;
grant, by the content computing device, the temporary remote access for the remote computing device to the data stored in the data storage during said communication session and while the authentication session remains valid; and
receiving, from the biometric sensor, a periodic keep-alive signal confirming that the communication session can continue, wherein the periodic keep-alive signal is received at a regular interval between consecutive receptions thereof,
wherein the content computing device is configured to be proximate to the biometric sensor or to integrally include the biometric sensor,
wherein the signal confirming biometric authentication comprises biometric data or a hash of the biometric data, and
wherein the periodic keep-alive signal comprises a subset of the biometric data less than a full set of the biometric data or a hash of a subset of the biometric data less than a full set of the biometric data.

15. A biometric sensor to enable temporary remote access using biometric data for authentication, the biometric sensor comprising:
an output configured to communicate to a content computing device, a signal confirming biometric authentication to thereby establish an authentication session, wherein:
the temporary remote access is to data stored in a data storage of the content computing device and is granted to a remote computing device during a communication session between the content computing device and the remote computing device and while the authentication session remains valid,
the biometric sensor is configured to be proximate to the content computing device or to be integrated with the content computing device, and
the authentication session is terminated unless renewed by the biometric sensor communicating a periodic keep-alive signal confirming that the communication session can continue, wherein the periodic keep-alive signal is communicated at a regular interval between consecutive communications thereof,
wherein the signal confirming biometric authentication comprises biometric data or a hash of the biometric data, and
wherein the periodic keep-alive signal comprises a subset of the biometric data less than a full set of the biometric data or a hash of a subset of the biometric data less than a full set of the biometric data.

16. A non-transitory computer readable storage medium storing a computer program comprising instructions which, when executed on at least one processor, cause the at least one processor to perform the method of claim 1.

17. The method of claim 1, wherein different receptions of the periodic keep-alive signal comprise different subsets of the biometric data.

18. The method of claim 8, wherein different communications of the periodic keep-alive signal comprise different subsets of the biometric data.

19. The content computing device of claim 14, wherein different receptions of the periodic keep-alive signal comprise different subsets of the biometric data.

20. The biometric sensor of claim 15, wherein different communications of the periodic keep-alive signal comprise different subsets of the biometric data.

* * * * *